United States Patent
Quintanar

(10) Patent No.: US 11,369,727 B2
(45) Date of Patent: Jun. 28, 2022

(54) PRESSURE CONTROL IN NEGATIVE PRESSURE WOUND THERAPY SYSTEMS

(71) Applicant: Smith & Nephew, Inc., Memphis, TN (US)

(72) Inventor: Felix Clarence Quintanar, Hull (GB)

(73) Assignee: Smith & Nephew, Inc., Memphis, TN (US)

( * ) Notice: Subject to any disclaimer, the term of this patent is extended or adjusted under 35 U.S.C. 154(b) by 169 days.

(21) Appl. No.: 16/493,540

(22) PCT Filed: Mar. 14, 2018

(86) PCT No.: PCT/US2018/022470
§ 371 (c)(1),
(2) Date: Sep. 12, 2019

(87) PCT Pub. No.: WO2018/170151
PCT Pub. Date: Sep. 20, 2018

(65) Prior Publication Data
US 2020/0000980 A1    Jan. 2, 2020

Related U.S. Application Data

(60) Provisional application No. 62/471,838, filed on Mar. 15, 2017.

(51) Int. Cl.
*A61M 1/00* (2006.01)

(52) U.S. Cl.
CPC .............. *A61M 1/743* (2021.05); *A61M 1/90* (2021.05); *A61M 2205/18* (2013.01);
(Continued)

(58) Field of Classification Search
CPC .......................... A61M 1/0031; A61M 1/0033
See application file for complete search history.

(56) References Cited

U.S. PATENT DOCUMENTS 5,158,529 A * 10/1992 Kanai ................... A61M 60/43
                                                          604/914
5,599,308 A    2/1997 Krupa
(Continued)

FOREIGN PATENT DOCUMENTS

EP          2529765 A2    12/2012
EP          2389961 B1     3/2013
(Continued)

OTHER PUBLICATIONS

International Search Report and Written Opinion, re PCT Application No. PCT/US2018/022470, dated May 30, 2018.
(Continued)

*Primary Examiner* — Adam Marcetich
(74) *Attorney, Agent, or Firm* — Knobbe, Martens, Olson & Bear, LLP

(57) ABSTRACT

Embodiments of negative pressure wound therapy systems and methods for operating the systems are disclosed. In some embodiments, a system includes a pump assembly, canister, and a wound dressing configured to be positioned over a wound. The pump assembly, canister, and the wound dressing can be fluidically connected to facilitate delivery of negative pressure to a wound. The system can additionally include a valve configured to control the introduction of positive pressure to the wound.

20 Claims, 11 Drawing Sheets

(52) U.S. Cl.
CPC . *A61M 2205/3344* (2013.01); *A61M 2205/50* (2013.01); *A61M 2205/505* (2013.01); *A61M 2205/583* (2013.01); *A61M 2205/7518* (2013.01)

(56) References Cited

U.S. PATENT DOCUMENTS

| | | | |
|---|---|---|---|
| 6,135,116 A * | 10/2000 | Vogel | A61M 1/90 |
| | | | 128/898 |
| 6,228,056 B1 | 5/2001 | Boehringer et al. | |
| 6,241,706 B1 * | 6/2001 | Leschinsky | A61M 60/40 |
| | | | 604/99.01 |
| 6,921,373 B1 * | 7/2005 | Bernstein | A61H 9/0078 |
| | | | 128/DIG. 20 |
| 7,004,915 B2 | 2/2006 | Boynton et al. | |
| 7,438,705 B2 | 10/2008 | Karpowicz et al. | |
| 7,553,306 B1 | 6/2009 | Hunt et al. | |
| 7,670,323 B2 | 3/2010 | Hunt et al. | |
| 7,753,894 B2 | 7/2010 | Blott et al. | |
| 8,202,262 B2 | 6/2012 | Lina et al. | |
| 8,235,955 B2 | 8/2012 | Blott et al. | |
| 8,366,692 B2 | 2/2013 | Weston | |
| 8,377,016 B2 | 2/2013 | Argenta et al. | |
| 8,494,349 B2 | 7/2013 | Gordon | |
| 8,905,985 B2 | 12/2014 | Allen et al. | |
| 9,023,002 B2 | 5/2015 | Robinson et al. | |
| 9,067,003 B2 | 6/2015 | Buan et al. | |
| 10,117,975 B2 | 11/2018 | Wall et al. | |
| 10,231,878 B2 | 3/2019 | Hartwell et al. | |
| 2002/0183659 A1 * | 12/2002 | Krause | A61H 9/005 |
| | | | 601/6 |
| 2003/0144690 A1 * | 7/2003 | Zheng | A61H 9/0078 |
| | | | 606/201 |
| 2003/0216672 A1 * | 11/2003 | Rastegar | A61H 9/0071 |
| | | | 601/9 |
| 2004/0064132 A1 | 4/2004 | Boehringer et al. | |
| 2006/0029675 A1 | 2/2006 | Ginther | |
| 2006/0149171 A1 | 7/2006 | Vogel et al. | |
| 2007/0118096 A1 | 5/2007 | Smith et al. | |
| 2008/0039761 A1 | 2/2008 | Heaton et al. | |
| 2008/0216898 A1 * | 9/2008 | Grant | A61M 1/1601 |
| | | | 137/154 |
| 2009/0043268 A1 | 2/2009 | Eddy et al. | |
| 2009/0082741 A1 | 3/2009 | Hu | |
| 2009/0171288 A1 | 7/2009 | Wheeler | |
| 2009/0299306 A1 | 12/2009 | Buan | |
| 2010/0022990 A1 | 1/2010 | Karpowicz et al. | |
| 2010/0042059 A1 | 2/2010 | Pratt et al. | |
| 2010/0063483 A1 * | 3/2010 | Adahan | A61M 1/962 |
| | | | 604/543 |
| 2010/0100075 A1 * | 4/2010 | Weston | A61M 1/73 |
| | | | 604/543 |
| 2010/0150991 A1 | 6/2010 | Bernstein | |
| 2010/0168687 A1 | 7/2010 | Yu | |
| 2010/0228205 A1 | 9/2010 | Hu et al. | |
| 2010/0274177 A1 | 10/2010 | Rybski et al. | |
| 2010/0298792 A1 * | 11/2010 | Weston | A61M 1/90 |
| | | | 604/319 |
| 2010/0312126 A1 * | 12/2010 | Williams | A61B 5/02156 |
| | | | 600/486 |
| 2011/0015585 A1 | 1/2011 | Svedman et al. | |
| 2011/0015593 A1 * | 1/2011 | Svedman | A61M 1/0031 |
| | | | 604/319 |
| 2011/0066096 A1 | 3/2011 | Svedman | |
| 2011/0112492 A1 | 5/2011 | Bharti et al. | |
| 2011/0257572 A1 | 10/2011 | Locke et al. | |
| 2012/0001762 A1 | 1/2012 | Turner et al. | |
| 2012/0035560 A1 | 2/2012 | Eddy et al. | |
| 2012/0046625 A1 | 2/2012 | Johannison | |
| 2012/0184930 A1 | 7/2012 | Johannison | |
| 2012/0271256 A1 * | 10/2012 | Locke | A61M 1/0066 |
| | | | 604/319 |
| 2013/0019744 A1 | 1/2013 | Hu | |
| 2013/0237889 A1 * | 9/2013 | Wright | A61H 9/0078 |
| | | | 601/149 |
| 2013/0245580 A1 | 9/2013 | Locke et al. | |
| 2013/0303975 A1 | 11/2013 | Gvodas, Jr. | |
| 2014/0163490 A1 * | 6/2014 | Locke | A61F 13/0206 |
| | | | 604/319 |
| 2014/0276547 A1 * | 9/2014 | Lonky | A61M 1/80 |
| | | | 604/503 |
| 2015/0025482 A1 * | 1/2015 | Begin | A61M 1/0001 |
| | | | 604/318 |
| 2015/0165182 A1 * | 6/2015 | Pratt | A61M 37/00 |
| | | | 604/290 |
| 2016/0287763 A1 * | 10/2016 | Simmons | A61M 1/96 |
| 2017/0354767 A1 * | 12/2017 | Carr | A61M 1/0025 |

FOREIGN PATENT DOCUMENTS

| | | |
|---|---|---|
| WO | WO 2003/005943 | 1/2003 |
| WO | WO-2008104609 A1 | 9/2008 |
| WO | WO-2008132215 A1 | 11/2008 |
| WO | WO-2009021523 A1 | 2/2009 |
| WO | WO-2009093116 A1 | 7/2009 |
| WO | WO-2011023275 A1 | 3/2011 |
| WO | WO 2018/170151 | 9/2018 |

OTHER PUBLICATIONS

Hartmann Vivano., "Vivano—Product Application Description," retrieved from http://www.vivanosystem.info/20809.php, accessed on Feb. 28, 2013, 3 pages.

International Preliminary Report on Patentability for Application No. PCT/US2018/022470, dated Sep. 26, 2019, 10 pages.

* cited by examiner

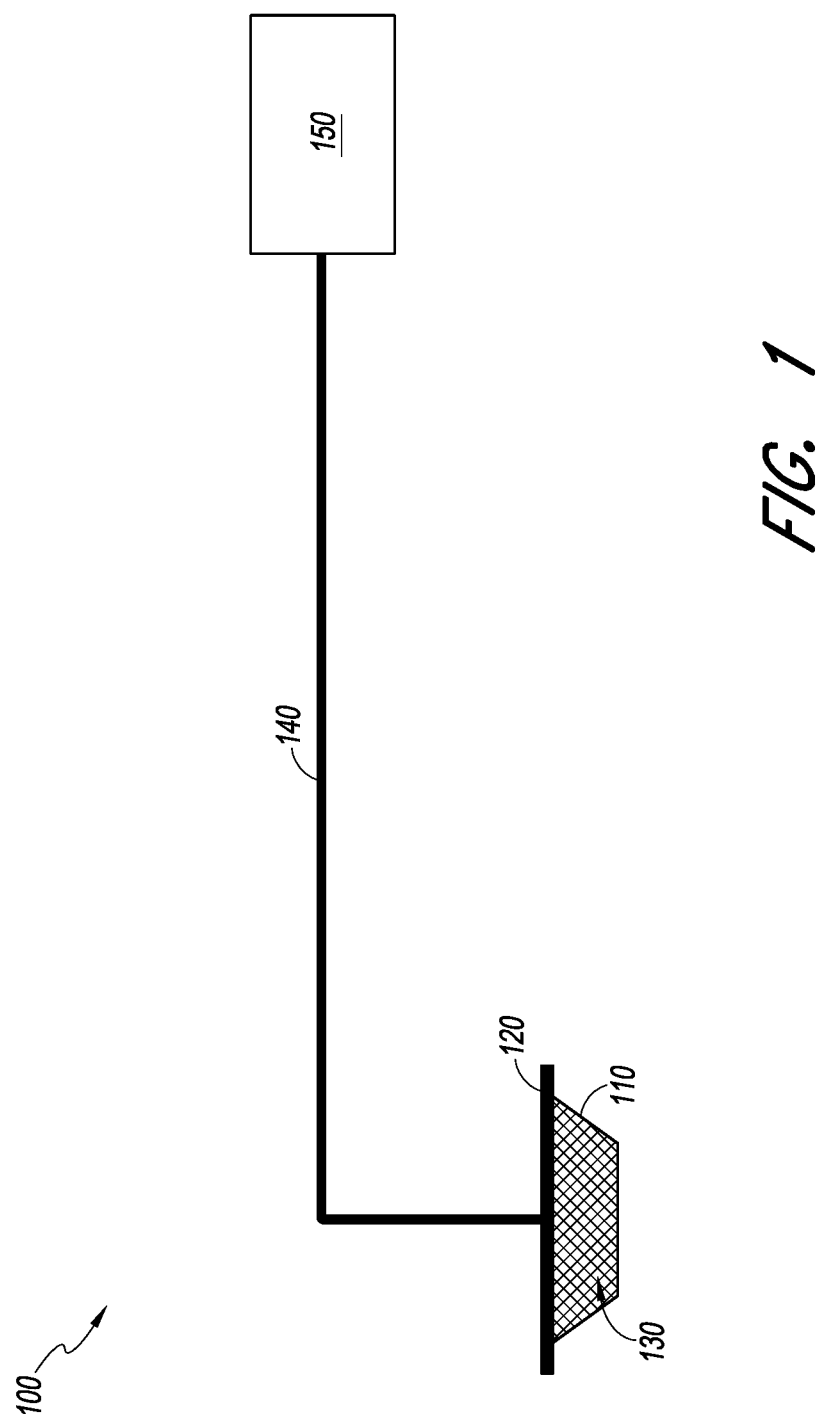

PRESSURE CONTROL IN NEGATIVE PRESSURE WOUND THERAPY SYSTEMS

CROSS-REFERENCE TO RELATED APPLICATIONS

This application is a U.S. national stage application of International Patent Application No. PCT/US2018/022470, filed Mar. 14, 2018, which claims the benefit of U.S. Provisional Application No. 62/471,838, filed Mar. 15, 2017; the disclosures of which are hereby incorporated by reference in their entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound is disclosed. The apparatus can include a source of negative pressure, a valve, and a controller. The source of negative pressure can be in fluidic communication via a flow path with a wound dressing placed over a wound. The source of negative pressure can provide negative pressure under the wound dressing. The valve can control supply of positive pressure via the flow path to the wound dressing. The controller can: operate the source of negative pressure to supply negative pressure via the flow path to the wound dressing, determine a pressure difference between a pressure under the wound dressing and a pressure setting, generate a control signal according at least to the pressure difference, and using the control signal, operate the valve to supply positive pressure via the flow path to the wound dressing so that the pressure under the wound dressing reaches the pressure setting.

The apparatus of the preceding paragraph can include one or more of the following features: The controller can operate the valve to supply positive pressure when the controller applies intermittent negative pressure wound therapy to the wound. The control signal can be a pulse-width modulation (PWM) signal, and the controller can vary a duty cycle of the PWM signal to operate the valve to supply positive pressure via the flow path to the wound dressing. The controller can generate the control signal using a proportional-integral-derivative (PID) calculation, and an error of the PID calculation can be the pressure difference. The controller can: at a first time, determine that an accumulated error of the PID calculation is negative, and set an integral term of the PID calculation to be 0 and the accumulated error to be 0 in response to a determination that the accumulated error is negative. The controller can: at a first time, determine that the error is negative, and set an accumulated error of the PID calculation to be greater than a sum of the accumulated error and the error in response to a determination that the error is negative. The valve can be positioned before an exhaust for the source of negative pressure. The valve can be a solenoid valve.

A method of operating or manufacturing the apparatus of the preceding two paragraphs is also disclosed.

In some embodiments, a method for applying negative pressure therapy to a wound is disclosed. The method can include: providing negative pressure via a flow path to a wound dressing placed over a wound; determining a pressure difference between a pressure under the wound dressing and a pressure setting; generating a control signal according at least to the pressure difference; and using the control signal, operating a valve to supply positive pressure via the flow path to the wound dressing so that the pressure under the wound dressing reaches the pressure setting.

The method of the preceding paragraph can include one or more of the following features: The operating the valve to supply positive pressure can be performed when intermittent negative pressure wound therapy is being applied to the wound. The control signal can be a pulse-width modulation (PWM) signal, and the operating the valve to supply positive pressure can be performed by varying a duty cycle of the PWM signal. The generating the control signal can include generating the control signal using a proportional-integral-derivative (PID) calculation, and an error of the PID calculation can be the pressure difference. The valve can be a solenoid valve.

BRIEF DESCRIPTION OF THE DRAWINGS

Embodiments of the present disclosure will now be described hereinafter, by way of example only, with reference to the accompanying drawings in which:

FIG. 1 illustrates a reduced pressure wound therapy system according to some embodiments.

DETAILED DESCRIPTION

Overview

Figure 2A:
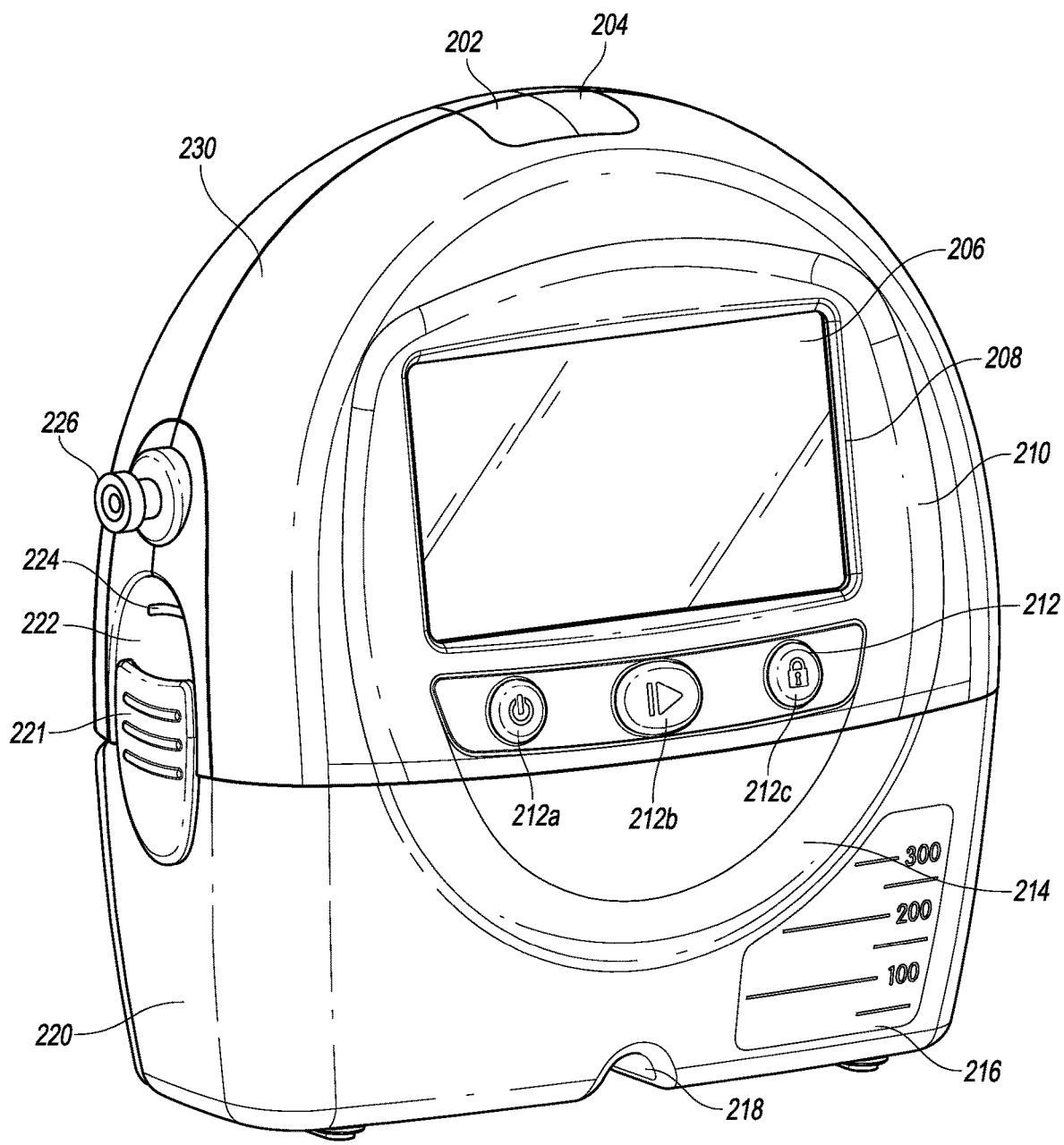
FIGS. 2A, 2B, and 2C illustrate a pump assembly and canister according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings, TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 mmHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg), Negative Pressure System FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

FIG. 2A illustrates a front view of a pump assembly 230 and canister 220 according to some embodiments. As is illustrated, the pump assembly 230 and the canister are connected, thereby forming a negative pressure wound therapy device. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons configured to allow the user to operate and monitor the operation of the TNP system. As is illustrated, there buttons 212a, 212b, and 212c (collectively referred to as buttons 212) are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230, The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
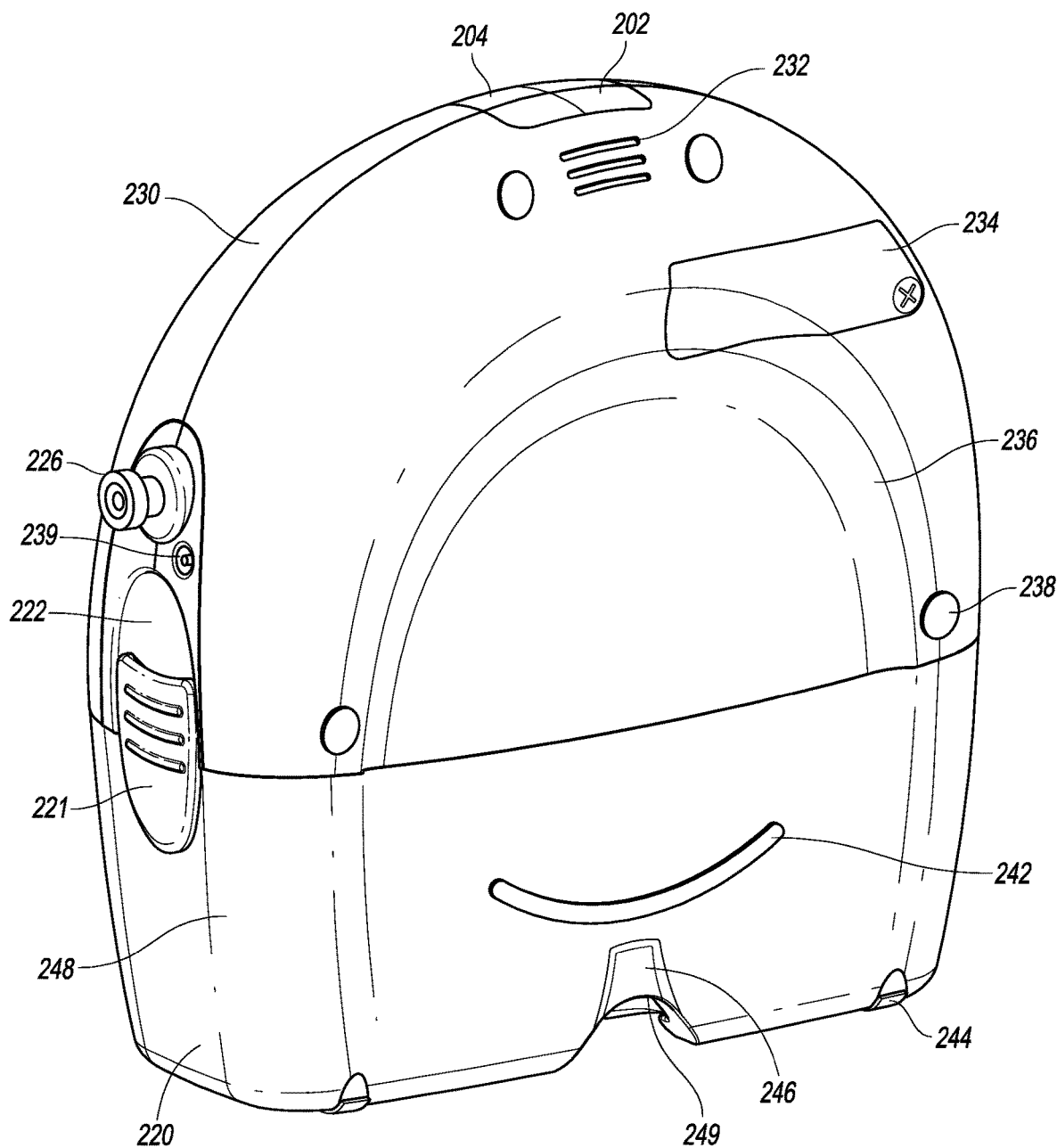

FIG. 2B illustrates a rear view of the pump assembly 230 and canister 220 according to some embodiments. The pump assembly 230 comprises a speaker port 232 for producing sound. The pump assembly 230 includes a filter access door 234 with a screw for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
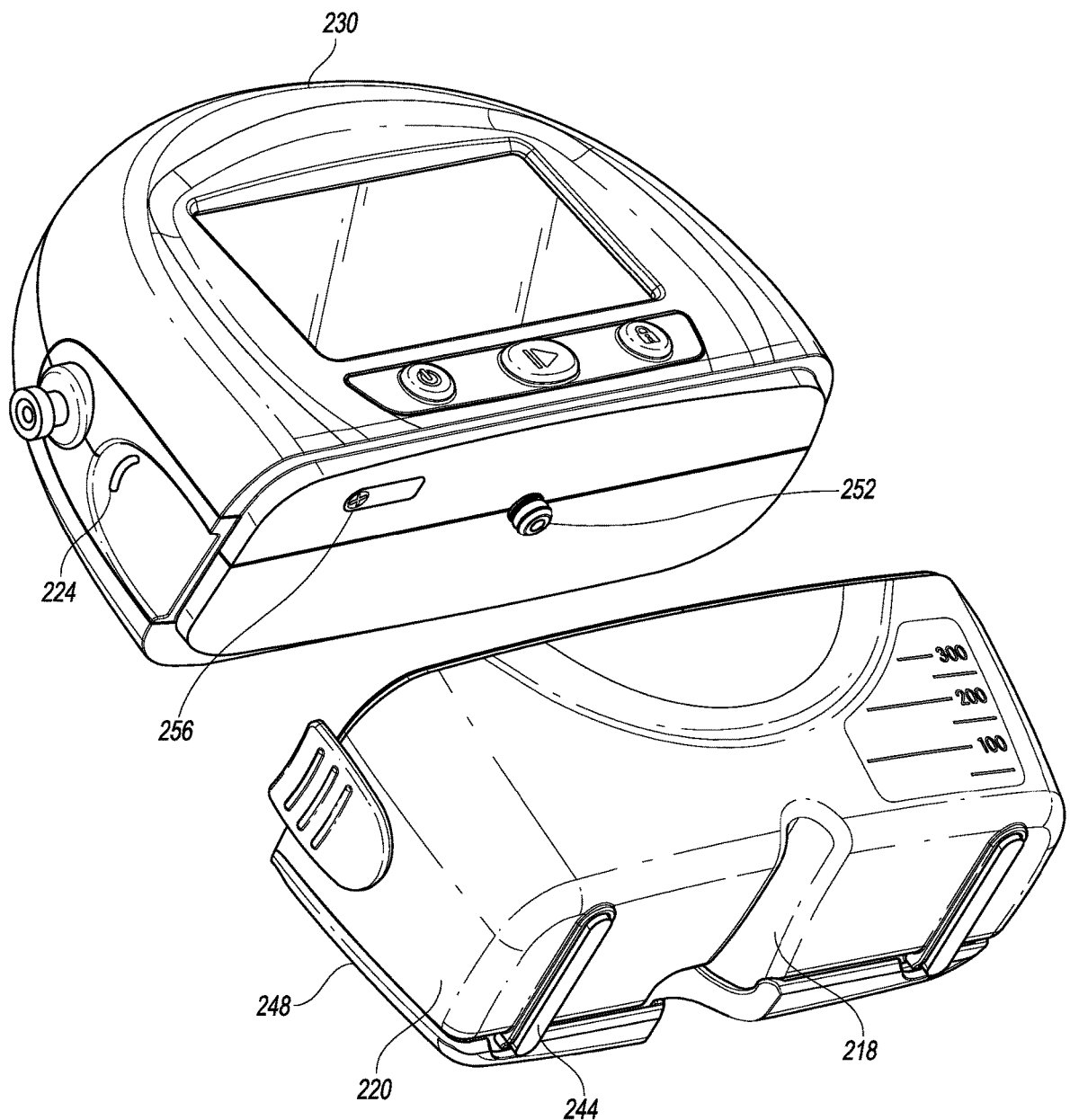

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, or hybrid data transfer interfaces, such as SD, Compact Disc (CD), DVD, FireWire, Thunderbolt, PCI Express, and the like. In other embodiments, one or more of these additional ports are accessed through the door 234.

Pump Assembly Electronics and Components

Figure 3A:
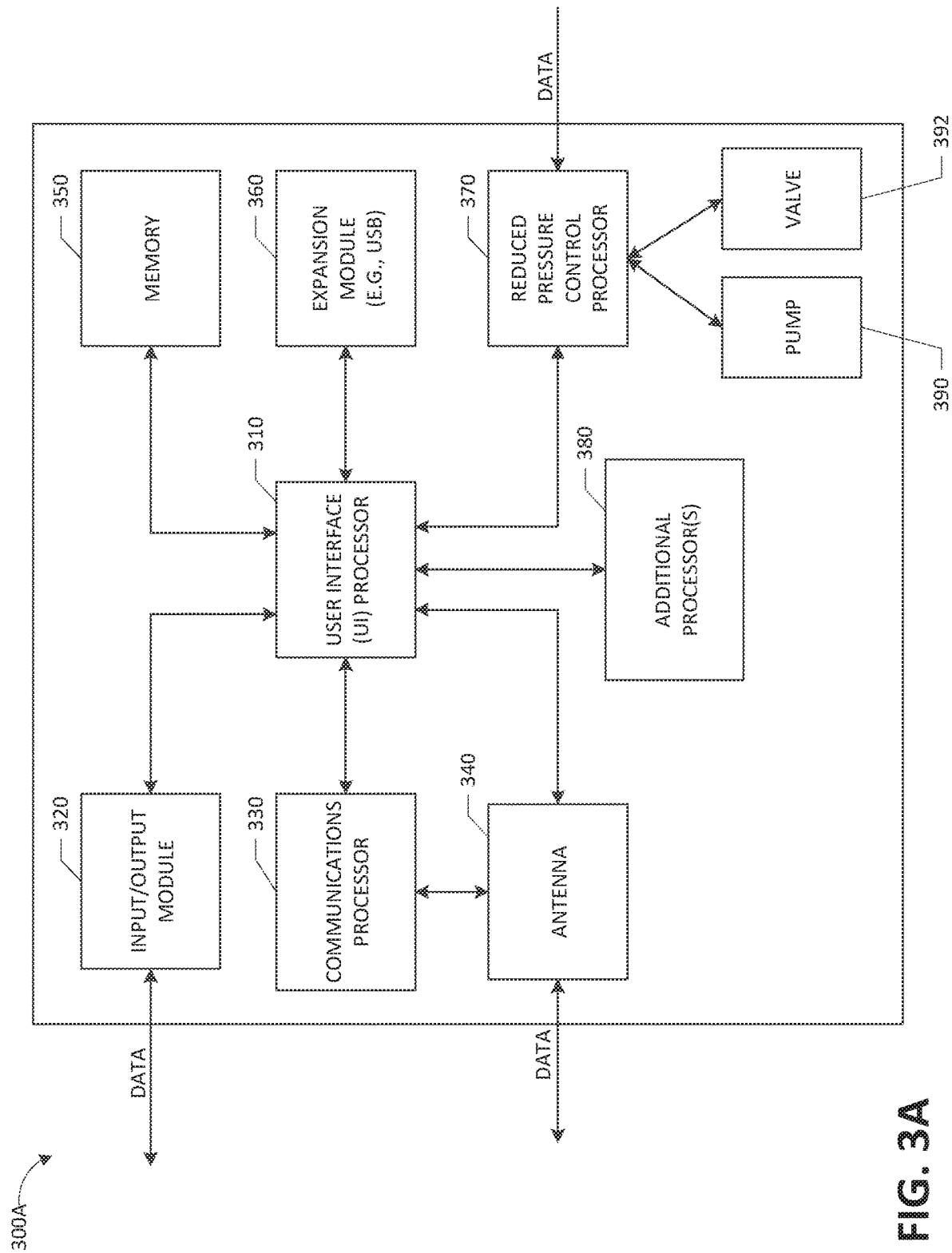
FIG. 3A illustrates an electrical component schematic of a pump assembly according to some embodiments.

FIG. 3A illustrates an electrical component schematic 300A of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors.

The pump assembly can comprise a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a reduced pressure control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The reduced pressure control processor 370 can be configured to control the operation of a reduced pressure source, such as a pump 390, and a valve 392. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The valve 392 can be a suitable valve, such as a solenoid valve, diaphragm valve, and the like, and be positioned, for instance, downstream (or before) an exhaust for the pump assembly or in a fluid flow path between the pump assembly and a wound dressing. The valve 392 can be a single valve or composed of multiple different valves.

The reduced pressure control processor 370 can measure pressure in a fluid flow path, using data received from one or more pressure sensors, calculate the rate of fluid flow, and control the pump 390 and the valve 392. The reduced pressure control processor 370 can control a pump motor of the pump 390 so that a desired level of negative pressure is achieved in the wound cavity 110. The desired level of negative pressure can be pressure set or selected by the user. In various embodiments, the reduced pressure control processor 370 controls the pump (e.g., pump motor) using pulse-width modulation (PWM). A control signal for driving the pump 390 can be a 0-100% duty cycle PWM signal. Moreover, the reduced pressure control processor 370 can control opening and closing of the valve 392 so that a desired level of negative pressure is achieved in the wound cavity 110. The desired level of negative pressure can be pressure set or selected by the user or set automatically according to a mode of operation or setting for the pump assembly. In various embodiments, the reduced pressure control processor 370 controls the opening and closing of the valve 392 using PWM. A control signal for controlling or driving the valve 392 can be a 0-100% duty cycle PWM signal.

The reduced pressure control processor 370 can perform flow rate calculations and detect various conditions in a flow path. The reduced pressure control processor 370 can communicate information to the processor 310. The reduced pressure control processor 370 can include internal memory or can utilize memory 350. The reduced pressure control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), WiFi connectivity, Internet connectivity, and the like, Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

In some embodiments, using the connectivity provided by the communications processor 330, the device can upload any of the data stored, maintained, or tracked by the pump assembly. The device can also download various operational data, such as therapy selection and parameters, firmware and software patches and upgrades, and the like.

Figure 3B:
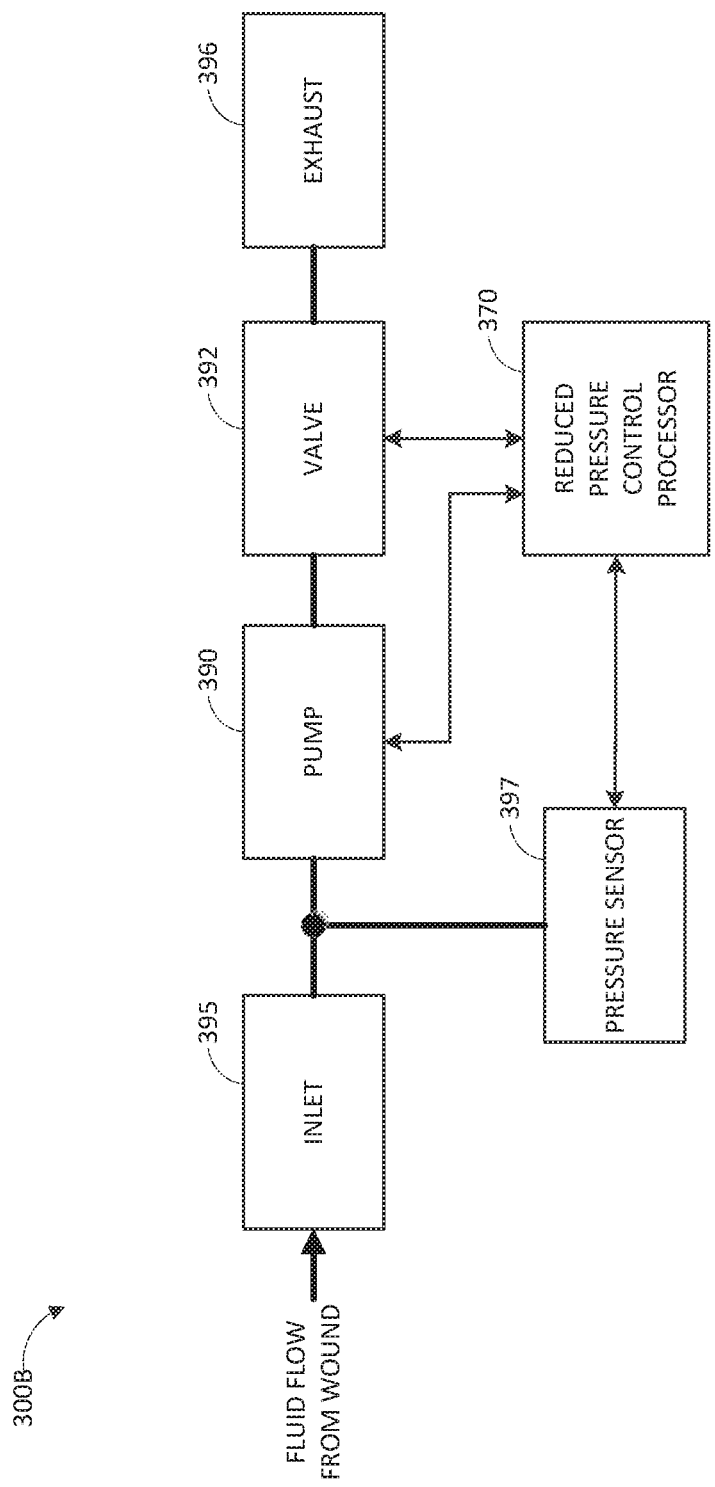
FIG. 3B illustrates a block diagram of components of a pump assembly according to some embodiments.

FIG. 3B illustrates a block diagram of certain components 300B of a pump assembly, such as the pump assembly 230, according to some embodiments. The components 300B include an inlet 395 (which can be like the inlet 252), the pump 390, the valve 392, an exhaust 396, a pressure sensor 397, and the reduced pressure control processor 370.

The pump 390 can provide negative pressure in a fluid flow path connecting the pump 390 (via the inlet 395) to a wound dressing placed over the wound, such that the negative pressure is provided to the inlet 395 and then to a wound dressing (for example, through a canister). The valve 392 can open (for example, partially or fully) to admit air, gas, or other fluid, which thereby provides positive pressure in the fluid flow path. In some implementations, the pump 390 under control of the reduced pressure control processor 370 can additionally or alternatively provide positive pressure in the fluid flow path, such as by operating the pump 390 in reverse. Additionally or alternatively, another pump different from the pump 390 and controllable by the reduced pressure control processor 370 can be included to provide positive pressure in the fluid flow path.

In some embodiments, the reduced pressure control processor 370 can measure the pressure in the fluid flow path near or at the inlet 395 (or at any other location in the fluid flow path, such as at the wound), using data received from one or more pressure sensors, such as the pressure sensor 397, calculate the rate of fluid flow, and control the pump 390 and the valve 392. The reduced pressure control processor 370 can, for instance, control one or more pump actuators, such as a pump motor of the pump 390, or one or more valve actuators, such as a solenoid of the valve 392, so that a desired level of negative (or positive) pressure is achieved at the wound. The desired level of negative pressure (or pressure setpoint) can be a pressure set or selected by the user or set automatically according to a mode of operation or setting for the pump assembly.

The components 300B can further include one or more additional sensors (not shown), such as a tachometer, positioned to detect or determine a level of activity of the pump 390 (for example, the pump motor) and provide indications responsive to the level of activity of the pump 390 to the reduced pressure control processor 370, For example, a tachometer can be separate from the pump 390 (for example, external to the pump) and positioned near or coupled to the pump 390, and the tachometer can detect a rotation (such as a partial rotation, complete rotation, or multiple partial or complete rotations) of a pump motor of the pump 390.

In some implementations, at least two pressure sensors can be positioned in or fluidically connected to the fluid flow path to permit differential measurement of the pressure. For example, a first pressure sensor can be positioned downstream of the wound dressing (such as at or near an inlet of the pump assembly) and a second pressure sensor can be positioned to detect pressure at or near the wound dressing or at or near a canister. This configuration can be accomplished by incorporating, in addition to one or more lumens forming a first fluid flow path connecting the pump assembly to the wound, a second fluid flow path that includes one or more lumens connecting the pump assembly to the wound dressing and through which the second pressure sensor can monitor pressure at or near the wound dressing or at or near the canister. The first and second fluid flow paths can be fluidically isolated from each other. When the at least two pressure sensors are used, the rate of change of pressure (for example, in peak-to-peak pressure or maximum pressure) in the first and second fluid flow paths can be determined and the difference in pressure detected between the first and second pressure sensors can be determined. These values can be used separately or together to detect various operational conditions, such as leaks, blockages, canister full, presence of blood in the first fluid flow path or the second fluid flow path, etc. Moreover, multiple redundant pressure sensors can be provided to protect against failure of one or more of the pressure sensors in some implementations.

Operation of the Pump Assembly

In some embodiments, the pump assembly 230 can be operated using a touchscreen interface displayed on the screen 206. Various graphical user interface (GUI) screens present information on systems settings and operations, among other things. The touchscreen interface can be actuated or operated by a finger (or a stylus or another suitable device). Tapping a touchscreen cam result in making a selection. To scroll, a user can touch screen and hold and drag to view the selections. Additional or alternative ways to operate the touchscreen interface can be implemented, such as multiple finger swipes for scrolling, multiple finger pinch for zooming, and the like.

Figure 4A:
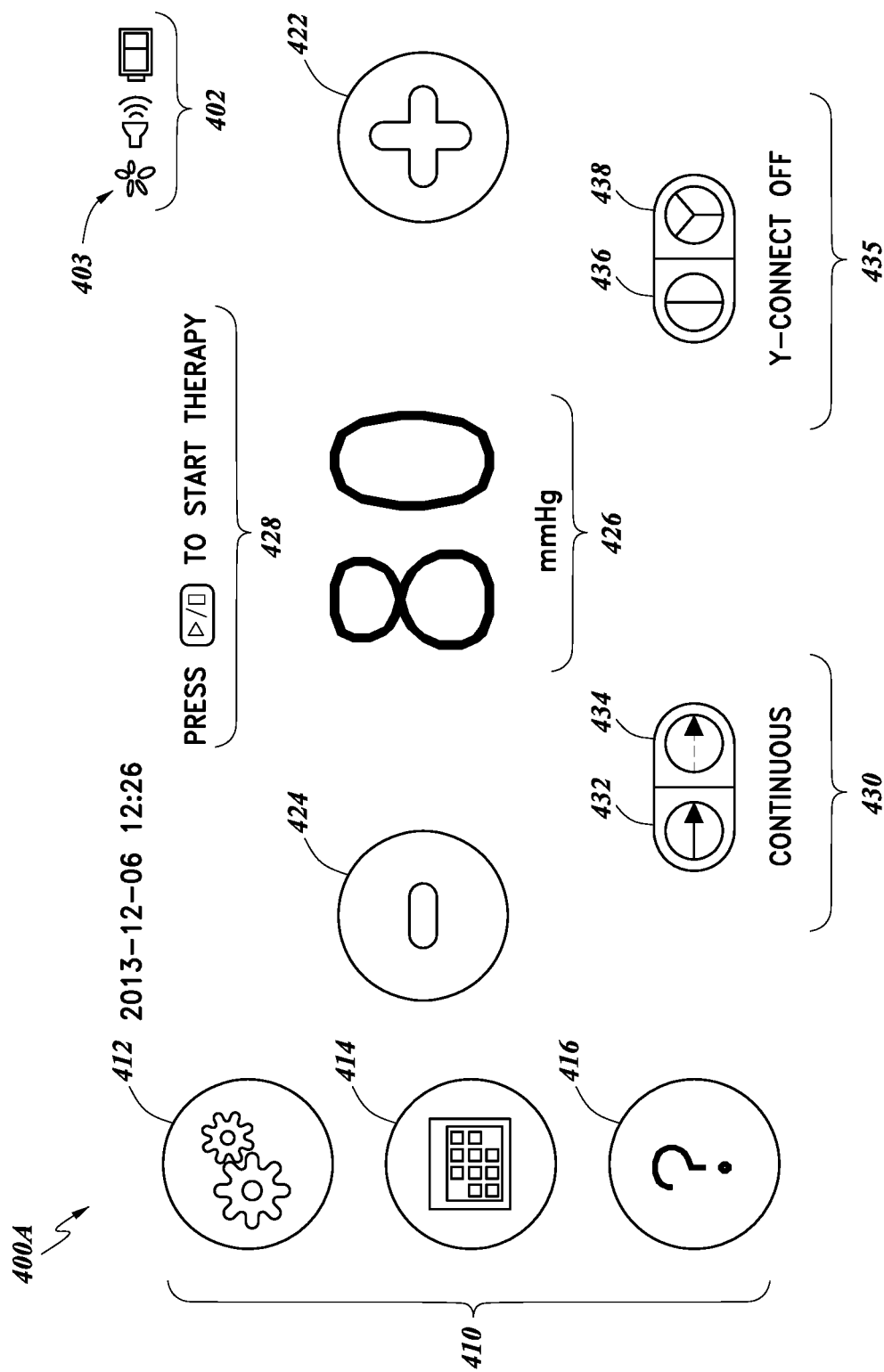
FIGS. 4A and 4B illustrate graphical user interface screens according to some embodiments.
Figure 4B:
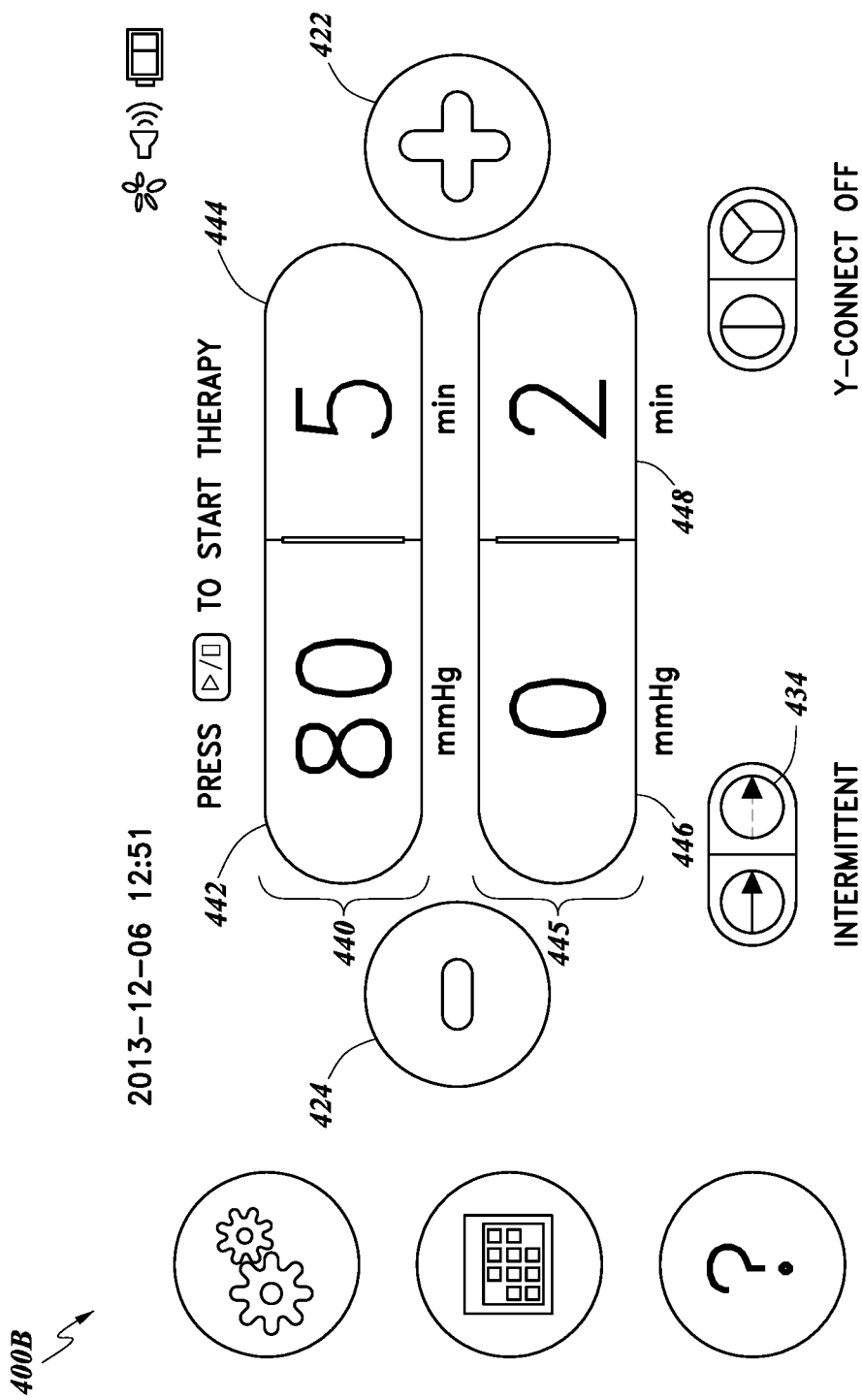

FIGS. 4A and 4B illustrate graphical user interface screens according to some embodiments. The GUI screens can be displayed on the screen 206, which can be configured as a touchscreen interface. Information displayed on the screens can be generated based on input received from the user. The GUI screens can be utilized for initializing the device, selecting and adjusting therapy settings, monitoring device operation, uploading data to the network (e.g., cloud), and the like. The illustrated GUI screens can be generated directly by an operating system running on the processor 310 or by a graphical user interface layer or component running on the operating system. For instance, the screens can be developed using Qt framework available from Digia.

FIG. 4A illustrates a therapy settings screen 400A according to some embodiments. The therapy settings screen 400A can be displayed after the pump assembly has been initialized (e.g., screen 400A can function as a home screen). The therapy settings screen 400A includes a status bar 402 that comprises icons indicating operational parameters of the device. Animated icon 403 is a therapy delivery indicator. When therapy is not being delivered, icon 403 can be static and displayed in a color, such as gray. When therapy is being delivered, icon 403 can turn a different color, such as orange, and becomes animated, such as, rotates, pulsates, become filled with color, etc. Other status bar icons include a volume indicator and a battery indicator, and may include additional icons, such as wireless connectivity. The therapy settings screen 400A includes date/time and information. The therapy settings screen 400A includes a menu 410 that comprises menu items 412 for accessing device settings, 414 for accessing logs, and 416 for accessing help. The pump assembly can be configured so that after a period of inactivity, such as not receiving input from the user, therapy settings screen 400A (or home screen) is displayed. Additional or alternative controls, indicators, messages, icons, and the like can be used.

The therapy settings screen 400A includes negative pressure up and down controls 422 and 424. Up and down controls 422 and 424 can be configured to adjust the negative pressure setpoint by a suitable step size, such as ±4 mmHg. As is indicated by label 426, the current therapy selection is −80 mmHg (or 80 mmHg below atmospheric pressure). The therapy settings screen 400A includes continuous/intermittent therapy selection 430, Continuous therapy selection screen can be accessed via control 432 and intermittent therapy selection screen can be accessed via control 434. As is illustrated, the current therapy setting is to continuously deliver negative pressure at −80 mmHg. As is indicated by message 428, therapy delivery can be initiated by pressing a button, such as button 212b on the pump assembly 230. The therapy settings screen 400A includes Y-connector selection 435 for treating multiple wounds, such as two, three, etc. wounds, with one pump assembly 230. Control 436 selects treatment of a single wound, and control 438 selects treatment of more than one wound by the pump assembly. As is indicated by the label "Y-CONNECT OFF," the current selection is to treat a single wound. Additional or alternative controls, indicators, messages, icons, and the like can be used.

FIG. 4B illustrates therapy settings screen 400B for delivering intermittent therapy according to some embodiments, Screen 400B can be accessed via control 434. Therapy settings screen 400B includes intermittent therapy settings 440 and 445. As is illustrated by settings of controls 442, 444, 446, and 448, respectively, current therapy selection is applying −80 mmHg of reduced pressure for 5 minutes followed by 2 minutes of applying atmospheric pressure (or turning off the vacuum pump). Such treatment cycles can be repeated until stopped by the user or by the pump assembly 230. Negative pressure levels and time durations can be adjusted by selecting one or more of controls 442, 444, 446, and 448 and operating the up or down controls 422 or 424 until desired values are selected. In some implementations, more than two negative pressure values and corresponding durations can be selected for treatment of a wound. For example, a user can select three or more negative pressure values and corresponding durations. Additional or alternative controls, indicators, messages, icons, and the like can be used.

Delivery of Negative Pressure Wound Therapy

In some embodiments, the pump assembly controls the vacuum pump to deliver negative pressure therapy to a wound according to a selected or programmed protocol. Pump control can be performed by the reduced pressure control processor 370 alone or in combination with the processor 310.

For example, the user can select continuous operation at a desired pressure (or negative pressure setpoint). The pump assembly can activate the vacuum pump to reduce or draw down the pressure at the wound (e.g., under the dressing) to reach the setpoint. As explained below, the drawdown can be performed by increasing the negative pressure at the wound limited by a maximum change in negative pressure per unit time called compression, until the setpoint (or another selected pressure value as explained below) has been achieved. Wound drawdown can be defined as the period of time immediately after therapy has been initiated during which the wound has not yet achieved the setpoint. As explained below, at the end of this period when the setpoint is achieved, the flow rate in the fluid flow path should be below a leak (or high flow) threshold and above a low vacuum threshold, otherwise an appropriate alarm will be activated.

As another example, the user can select intermittent operation between two desired pressures (or high and low pressure setpoints). The pump assembly can activate the vacuum pump to reduce or draw down the pressure at the wound to reach the high setpoint. Subsequently, the pump assembly can allow pressure at the wound to increase to reach the low setpoint. As explained below, decreasing and increasing negative pressure can be performed in accordance with the compression setting.

As yet another example, compression can be used anytime there is a change in the pressure setpoint (which can include stopping delivery of negative pressure). In some embodiments, different compression settings can be used for setpoint changes that result in decreasing or increasing pressure at the wound. In various embodiments, compression setting can be adjusted while a pressure setpoint is being achieved.

Figure 5:
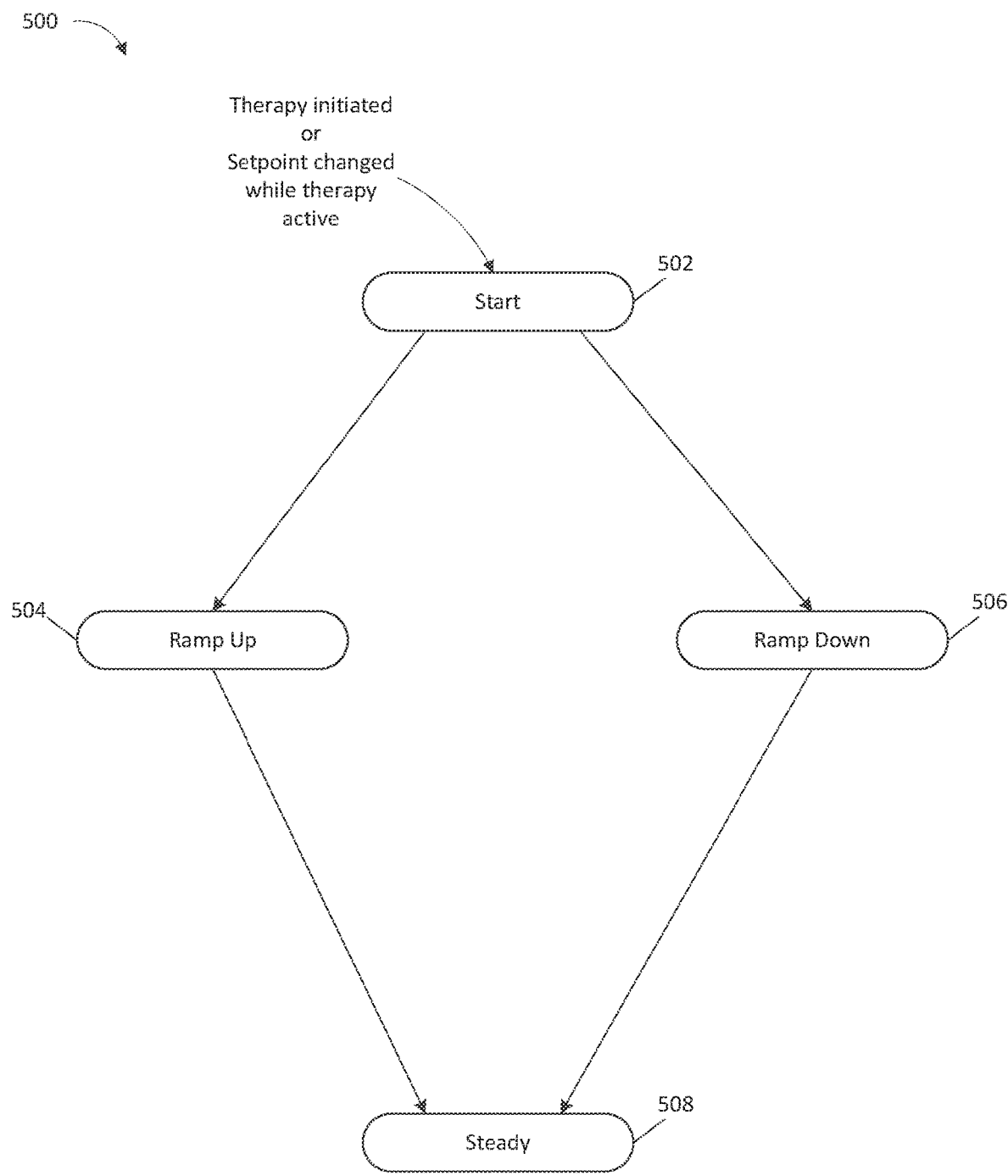
FIG. 5 illustrates a process of providing negative pressure wound therapy according to some embodiments.

FIG. 5 illustrates a process 500 for providing negative pressure wound therapy according to some embodiments. The process 500 can be executed by the reduced pressure control processor 370 alone or in combination with the processor 310 and utilize one or more other components described herein or other systems not shown. The process 500 can be periodically executed, such as for example every 100 milliseconds (or 10 times per second) or at any other suitable frequency. Alternatively or additionally, the process 500 can be continuously executed.

The process 500 can begin in block 502, which it can transition to when therapy is initiated or when the setpoint is changed while therapy is being delivered. In block 502, the process 500 compares wound pressure, which can be determined as explained below, to the setpoint. For example, the process 500 can subtract the wound pressure from the setpoint or vice versa. If the wound pressure is below the setpoint, the process 500 can transition to block 504. Conversely, if the wound pressure exceeds or is equal to the setpoint, the process 500 can transition to block 506.

In block 504 (pressure ramp up), the process 500 can increment a pump ramp setpoint by an amount that depends on the compression setting as explained below. The vacuum pump will then attempt to draw down (or make more negative) the wound pressure to reach the current value of the pump ramp setpoint. For example, a suitable pump drive signal, such as voltage or current signal, can be generated and supplied to the pump motor so as to increase the speed of the pump motor to achieve wound draw down. For purposes of efficiency, the pump motor can be driven using PWM or any other suitable method. The process 500 can continue incrementing the pump ramp setpoint until it reaches the setpoint selected by the user. The process 500 can transition to block 508 when the wound pressure has nearly reached or reached the setpoint, which can correspond to reaching steady state pressure under the wound dressing. For example, the process 500 can transition to block 508 when the wound pressure is within a ramp up threshold pressure of the setpoint, such as within 2 mmHg of the setpoint or within any other suitable value. In some embodiments, the pump ramp setpoint can be adaptively set to a higher negative pressure than the setpoint. For example, as is explained below, the device can detect presence of one or more leaks which result in a higher level of flow. Because this can cause loss of pressure at the wound, the device can compensate such loss of pressure by increasing the pump ramp setpoint above the setpoint. For instance, the device can set the pump ramp setpoint to be 1%, 2%, 5%, etc. more negative than the setpoint. In certain embodiments, the pump ramp setpoint can be adaptively set to a lower negative pressure (or more positive pressure) than the setpoint.

In block 506 (pressure ramp down), the process 500 can set the pump ramp setpoint to the setpoint selected by the user (or to another set value as explained above). The process 500 can deactivate the pump so that the wound pressure is allowed to decay, such as due to one or more leaks in the fluid flow path, to reach or almost reach the setpoint. This can be performed in accordance with the compression setting, such as for example, deactivating the pump for a first period of time and then activating the pump for a second period of time so that pressure at the wound increases according to the compression setting.

Figure 7:
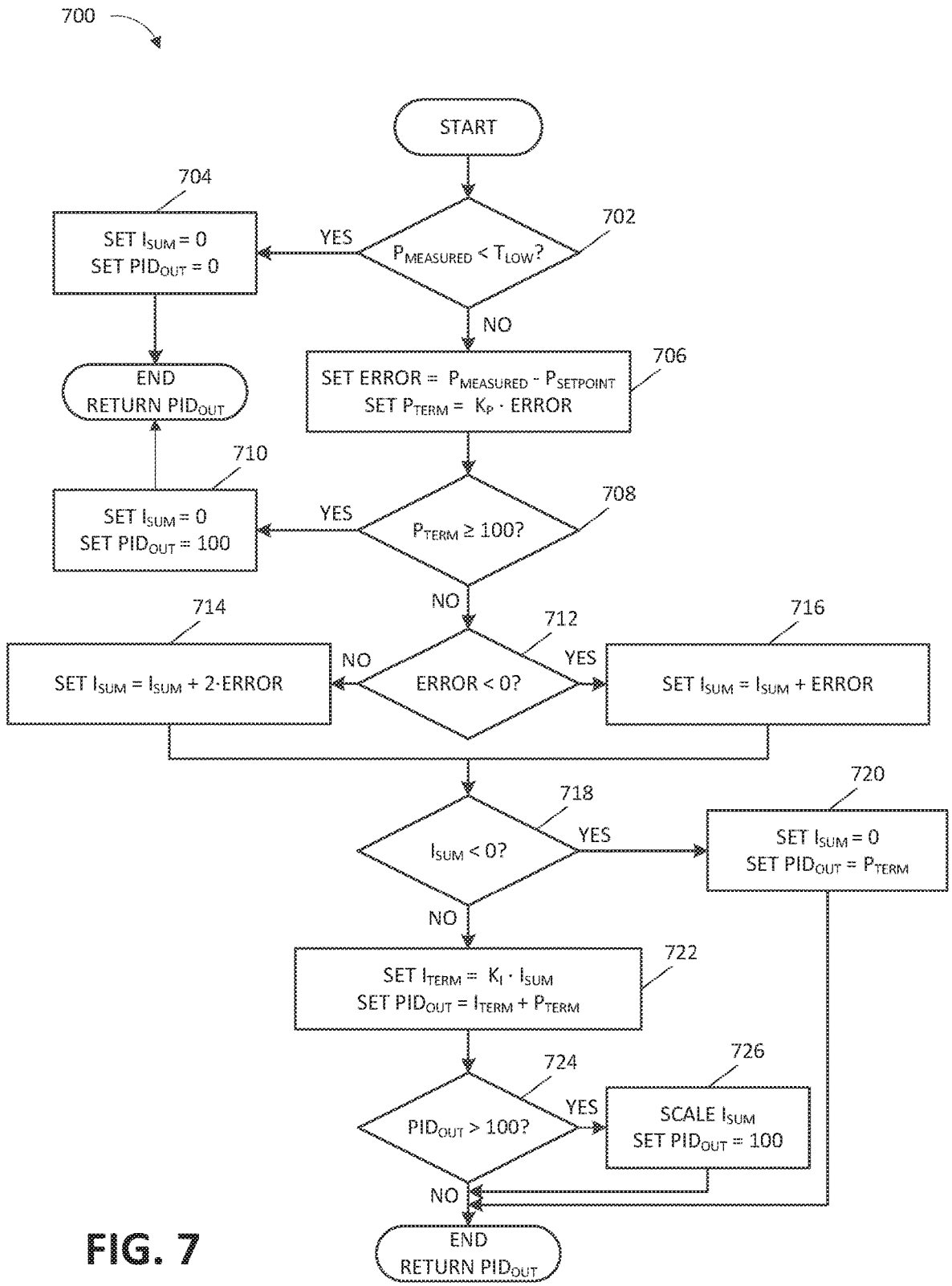
FIG. 7 illustrates a process for determining a duty cycle for a control signal for a source of positive pressure according to some embodiments.

Additionally or alternatively, the process 500 can open and close one or more valves (for example, the valve 392) positioned in the fluid flow path, such as described with respect to FIGS. 7 and 8, to thereby admit ambient air, gas, or another fluid into the fluid flow path in order to reach or almost reach the setpoint. This can be performed in accordance with the compression setting, such as for example opening the one or more valves for a first period of time and then closing some or all of the one or more valves for a second period of time so that pressure at the wound increases according to the compression setting. Further, the process 500 can operate a positive pressure pump to increase the pressure at the wound. Also, the process 500 can utilize a reservoir configured to store air or gas to increase the pressure at the wound. This is described in more detail in U.S. Pat. No. 8,366,692, which is incorporated by reference in its entirety. Such approaches can advantageously, in certain embodiments, enable negative pressure to be quickly reduced or relieved if appropriate, such as for patient safety in the case of bleeding, excessive pain, and the like.

At this point, the process 500 can transition to block 508. For example, the process 500 can transition to block 508 when the wound pressure is within a ramp down threshold pressure of the setpoint, such as within 5 mmHg of the setpoint or within any other suitable value. In some cases, the ramp down threshold pressure can be the same as the ramp up threshold pressure. In some embodiments, the pump ramp setpoint can be adaptively set to a lower negative pressure than the setpoint. For example, as is explained below, the device can detect presence of one or more leaks which result in a higher level of flow. Because this can cause loss of pressure at the wound, the device can compensate such loss of pressure by decreasing the pump ramp setpoint below the setpoint. For instance, the device can set the pump ramp setpoint to be 1%, 2%, 5%, etc. less negative than the setpoint. In certain embodiments, the pump ramp setpoint can be adaptively set to a higher negative pressure (or more positive pressure) than the setpoint.

In block 508 (steady state), the pump ramp setpoint can be set to the setpoint selected by the user (or another suitable value). The process 500 can control the vacuum pump to maintain the desired negative pressure at the wound. One or more conditions, such as high vacuum, low vacuum, leak, and the like can be detected in block 508 as is explained below. If the user changes the setpoint to be more negative or more positive or if delivery of therapy is paused, the process 500 can transition to block 502.

In some embodiments, the pump assembly controls the vacuum pump to draw down the wound (e.g., as is explained above in connection with block 504) by utilizing compression. Using compression can be beneficial for avoiding rapid changes in wound pressure, which can minimize patient pain or discomfort, reduce noise produced as a result of operating the pump, maintain efficient delivery of negative pressure, maintain efficient use of power (e.g., battery power), and the like. Compression can be executed by the process 500, which in turn can be implemented by the reduced pressure control processor 370 alone or in combination with the processor 310. Compression can correspond to the maximum desired increase or decrease in negative pressure at the wound per unit of time. Compression can be determined based on the negative pressure setpoint in the continuous mode or low and high negative pressure setpoints in the intermittent mode and selected compression setting (e.g., low, medium, or high).

Compression can be utilized when the wound is expected to experience a significant increase in negative pressure. This can occur when: (1) therapy is initiated on a deflated wound, and negative pressure will increase from zero or substantially zero to reach the pressure setpoint at the wound; (2) therapy is active in intermittent mode and during transitions from a low negative pressure setpoint to a high negative pressure setpoint, negative pressure will increase to reach the high pressure setpoint at the wound; (3) therapy is active in intermittent mode and during transitions from a high negative pressure setpoint to a low negative pressure setpoint, negative pressure will decrease to reach the low pressure setpoint at the wound; (4) therapy is active and the setpoint has been changed to a more negative pressure value, which will cause negative pressure to be increased to reach the higher pressure setpoint at the wound; (5) therapy is active and the setpoint has been changed to a more positive pressure value, which will cause negative pressure to be decreased to reach the lower pressure setpoint at the wound; (6) therapy is active and is stopped or paused for a period of time, which will cause the pressure to be gradually restored to atmospheric pressure; or (7) positive pressure is applied to the wound. Additional situations in which compression may be utilized include, for example, when a leak is introduced after seal has been achieved, which can cause negative pressure at the wound to rapidly drop and the vacuum pump to increase or ramp up delivery of negative pressure in an attempt to maintain pressure. Once the leak has been corrected, the pump would attempt to rapidly restore setpoint pressure at the wound according to the compression setting.

Compression can be achieved by maintaining a secondary negative pressure setpoint target that represents the negative pressure setpoint allowed by compression as a function of time. The secondary setpoint can correspond to the pump ramp setpoint. Secondary setpoint can be incremented or decremented based on the selected compression setting. Secondary setpoint can be incremented or decremented by a suitable amount every time process 500 is executed, such as 10 times a second or any other suitable frequency. For example, if low compression setting has been selected, the secondary setpoint can be incremented by −0.6 mmHg (or decremented by 0.6 mmHg), which can result in negative pressure ramp up (or ramp down) of no more than approximately −8 mmHg (or 8 mmHg) per second (assuming that pump rate is incremented 10 times a second, such as a result of executing the process 500). If medium compression setting has been selected, the secondary setpoint can be incremented by −2 mmHg (or decremented by 2 mmHg), which can result in negative pressure ramp up (or ramp down) of no more than approximately −20 mmHg (or 20 mmHg) per second. If high compression setting has been selected, the secondary setpoint can be incremented by −4 mmHg (or decremented by 4 mmHg), which can result is negative pressure ramp up (or ramp down) of no more than approximately −40 mmHg (or 40 mmHg) per second. These values are illustrative and any other suitable values can be used.

In some embodiments, the pump assembly monitors various parameters, such as pressure and rate of flow in the fluid flow path, in order to control the pump in connection with delivery of negative pressure wound therapy. Parameters monitoring and pump control can be performed by the reduced pressure control processor 370 alone or in combination with the processor 310. Monitoring the flow rate can be used, among other things, to ensure that therapy is properly delivered to the wound, to detect leakages, blockages, high pressure, and low vacuum, canister full, and the like.

The pump assembly can be configured to indirectly measure the flow rate in the fluid flow path. For example, the pump assembly can measure the speed (e.g., as frequency) of the vacuum pump motor by using a tachometer. Alternatively or additionally, the pump assembly can measure a level of activity or duty cycle of the pump using any suitable approach, such as by monitoring voltage or current supplied to the pump, sensing pump speed (e.g., by using a Hall sensor), measuring back EMF generated by the pump motor, and the like. Tachometer readings can be averaged in order to mitigate the effects of one or more errant readings. A number of most recent tachometer readings, such as over last 2.5 seconds or any other suitable time period, can be averaged to obtain short tachometer average. A number of less recent tachometer readings, such as over the last 30 seconds or any other suitable time period, can be averaged to obtain long tachometer average. Short and long tachometer averages can be utilized for pump control. Additionally or alternatively, the pump assembly can directly measure the flow rate, such as by using a flow meter.

Flow rate can be estimated as the air or gas volume moving over the wound per unit of time normalized to standard temperature and standard pressure (e.g., 1 atm), Flow rate can be periodically computed, such as every 250 milliseconds or any other suitable time value, according to the following formula:

$$\text{Flow Rate} = \text{Slope} * \text{Tachometer} + \text{Intercept}$$

Tachometer is short tachometer average (e.g., in Hz) and Slope and Intercept are constants that are based on the pressure setpoint. The values for Slope and Intercept can be determined for possible pressure setpoints (e.g., −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg) for a given vacuum pump type. The flow as a function of the pump speed may not be a best fit as a single line because the vacuum pump can be designed to be more efficient at lower flow rates. Because of this, slope and intercept values can be pre-computed for various setpoints and various pumps. Flow rate can be measured in standard liters per minute (SLPM) or any other suitable measurement unit. As explained below, the determined flow rate can be compared to various flow rate thresholds, such as blockage threshold, leakage threshold, and maximum flow rate threshold, to determine a presence of a particular condition, such as a blockage, leakage, over vacuum, etc.

In addition, the pump assembly can determine and monitor pressure in the flow path using one or more sensors. In some embodiments, the pump assembly includes a pressure sensor in or near the inlet 252 (or canister connection) of the pump assembly 230 or in any other suitable locations in the fluid flow path, such as described herein. This pressure sensor can measure the pressure in the canister (or in or near the dressing in a canisterless system). The arrangement of one or more pressure sensors in disclosed in U.S. Patent Publication No. 2015/0025482, which is incorporated by reference in its entirety. The pump assembly can continuously measure pressure in the canister, such as every millisecond or any other suitable duration. A suitable number of latest pressure sensor readings can be averaged to mitigate the effects of one or more errant readings.

Wound pressure can be estimated using the measured canister pressure and the pump speed, Because of presence of one or more leaks in the flow path, wound pressure may not be the same as canister pressure. For example, wound pressure may be lower or more positive than canister pressure. In some embodiments, wound pressure is estimated using the following formula:

$$\text{Wound Pressure} = \text{Canister Pressure} - (\text{Slope} * \text{Tachometer} + \text{Intercept})$$

Canister Pressure is averaged measured canister pressure. As explained above, Tachometer is short tachometer average and Slope and Intercept are constants that are based on the pressure setpoint. The values for Slope and Intercept are not necessarily same value as used above for determining the flow rate. Additionally or alternatively, wound pressure can be measured directly by a pressure sensor placed in the wound or near the wound or under the dressing.

Based on the determined flow rate, canister pressure, and wound pressure values, the pump assembly can monitor and detect various operating conditions. One or more of these conditions can be detected by the process 500 while the process in in block 508, Blockage in the fluid flow path can be determined by comparing the flow rate, as reflected by long tachometer average, to a particular blockage threshold over or during a period of time, such as 2 minutes or any other suitable duration. The blockage threshold can be selected or determined based on the particular pressure setpoint, That is, to detect blockage, the pump assembly can utilize a plurality of blockage thresholds corresponding to particular pressure setpoints. As explained above, the flow rate can be indirectly determined by detecting and monitoring the pump speed. Long tachometer average can be compared to the blockage threshold. Alternatively or additionally, short tachometer average or any other suitable measure of flow rate can be compared to the blockage threshold.

In some embodiments, blockage detection may be suspended while the process 500 is in block 506. That is, blockage detection can be configured to be suppressed or disabled when the therapy unit is in the ramp down state in block 506. Blockage detection can be enabled or re-enabled when the process transitions to another state, such as the steady state in block 508. In some embodiments, blockage detection can be disabled when the process 500 is in a state other than the ramp down state in block 506, such as when the process 500 is in the ramp up state in block 504, and re-enabled when the process 500 is in a state other than the steady state in block 508. In some embodiments, the process 500 can continuously monitor for a blockage condition, but when such conditions is detected, the process 500 can be configured to suppress the blockage alarm when in, for example, a pressure ramp down state.

When the pump is off, such as when intermittent therapy is applied with one of the pressure setpoints being set to zero, and negative pressure at the wound is expected to decrease (or become more positive) due to leaks, blockage can be detected by determining whether the pressure level at the wound is decreasing or decaying as expected. For example, the drop in pressure at the wound can be computed over a period of time, such as 30 seconds or any other suitable duration. A blockage may be present if the wound pressure at the end of the period of time has not decreased to satisfy (e.g., exceed) a pressure decay threshold.

In additional or alternative embodiments, multiple pressure sensors can be placed in the fluid flow path to facilitate detection of one or more of the above-described conditions. For example, in addition to or instead of the pressure sensor being placed in the pump inlet, a pressure sensor can be placed in the wound or under the dressing to directly determine the wound pressure. Measuring pressure at different locations in the fluid flow path, such as in the canister and at the wound, can facilitate detection of blockages, leaks, canister full condition, and the like. Multiple lumens can be utilized for connecting fluid flow path elements, such as pressure sensors, canister, pump assembly, dressing, and the like. Canister full condition can be detected by placing a sensor, such as capacitive sensor, in the canister. In some embodiments, in order to prevent occurrence of over vacuum, the maximum pressure supplied by the pump can be limited mechanically or electrically. For example, a pump drive signal, such as voltage or current supplied to the pump, can be limited not exceed a maximum flow rate threshold, such as 1.6 liters/min or any other suitable value. Additional details of flow rate detection and pump control are provided in U.S. Patent Publication No. 2013/0150813, which is incorporated by reference in its entirety.

In some embodiments, one or more flow sensors or flow meters can be used to directly measure the fluid flow. In some embodiments, the pump assembly can utilize one or more of the above-described techniques in parallel to control the pump and to detect various conditions. The pump assembly can be configured to suitably arbitrate between using parameters determined by different techniques. For example, the pump assembly can arbitrate between flow rates determined indirectly, such as based on the pump speed as measured by a tachometer, and directly, such as by using a flow meter. In certain embodiments, the pump assembly can indirectly determine the flow rate and resort to direct determination of the flow rate when needed, such as when indirectly determined flow rate is perceived to be inaccurate or unreliable.

Figure 6:
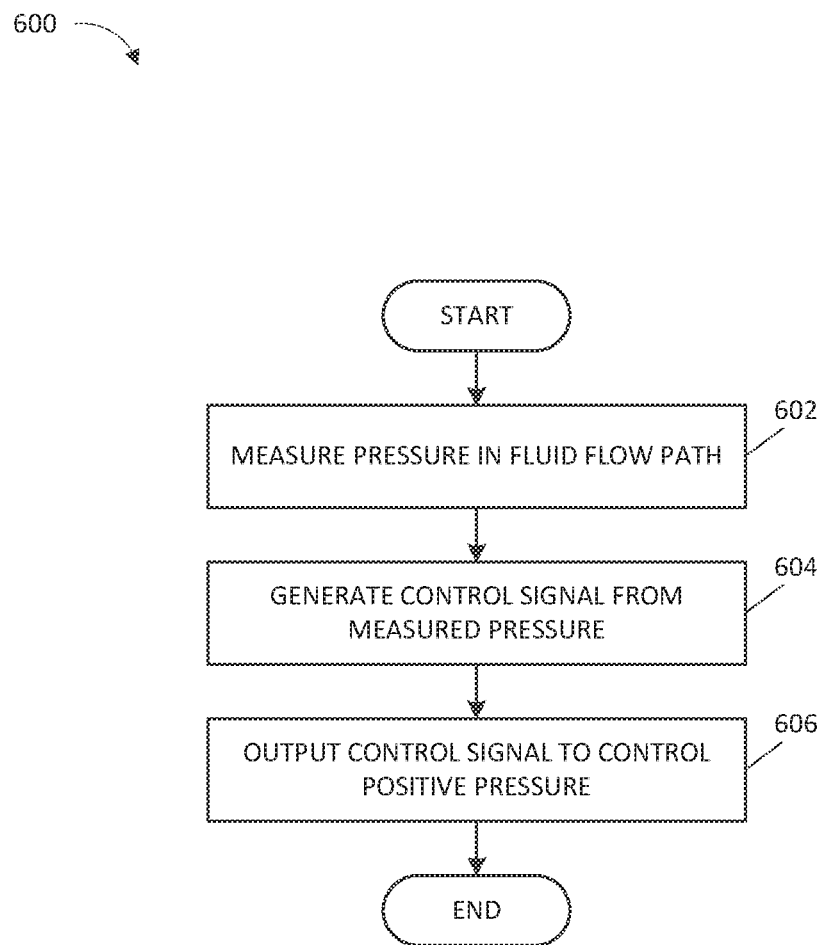
FIG. 6 illustrates a process of controlling wound therapy according to some embodiments.

FIG. 6 illustrates a process 600 of controlling wound therapy according to some embodiments. The process 600 can be executed by the reduced pressure control processor 370 alone or in combination with the processor 310 and utilize one or more other components described herein or other systems not shown. The process 600 can be periodically executed or at any other suitable frequency or continuously. Advantageously, in certain embodiments, the process 600 can enable dynamic control of the supply of positive pressure by a valve or a pressure source to a wound dressing. Such control can desirably allow for enhanced intermittent or dynamic therapies and control of therapy in a manner that reduces an amount of pain felt by a patient during negative pressure wound therapy.

At block 602, the process 600 can measure pressure in a fluid flow path. For example, the pressure may have been measured using the pressure sensor 397 at or near the inlet 395 or at any other suitable portion of the fluid flow path.

At block 604, the process 600 can generate a control signal from the measured pressure. For example, the control signal can be a PWM signal, and a duty cycle of the control signal can be varied according to the measured pressure. In some embodiments, the duty cycle of the control signal can be varied according to a proportional-integral-derivative (PID) calculation that depends on a difference between the measured pressure and a pressure setpoint, such as is described with respect to the process 700 of FIG. 7.

At block 606, the process 600 can output the control signal to control positive pressure. For example, the control signal can be output to the valve 392 to operate the valve 392 to vary an amount of positive pressure provided to the fluid flow path.

FIG. 7 illustrates a process 700 for determining a duty cycle for a PWM control signal for a positive pressure source, such as the valve 392, according to some embodiments. The process 700 can be executed by the reduced pressure control processor 370 alone or in combination with the processor 310 and utilize one or more other components described herein or other systems not shown. The process 700 can be executed in intermittent pressure mode when positive pressure is provided to the wound (for example, in block 506 of FIG. 5). The process 700 can be periodically executed or at any other suitable frequency or can be performed when positive pressure is introduced under control of a pump assembly. Advantageously, in certain embodiments, the process 700 can enable the reduced pressure control processor 370 to determine a suitable duty cycle for controlling a source of positive pressure, such as a valve like the valve 392 or a pump like the pump 390 operating in reverse or a dedicated positive pressure pump to provide positive pressure, so that an amount of positive pressure provided is ramped, provided according to a compression setting, or controlled to a setpoint.

The process 700 can be based on a PID calculation and serve as a control loop feedback mechanism. The control loop feedback mechanism can provide up to three-term control according to an error value calculated based on a difference between a measured pressure and a setpoint pressure. The up to three-term control can be determined by a proportional control term ($P_{TERM}$), integral control term ($I_{TERM}$), or derivative control term ($D_{TERM}$). In some embodiments, the output of the PID calculation ($PID_{OUT}$) can depend on a sum of $P_{TERM}$, $I_{TERM}$, and $D_{TERM}$. The $I_{TERM}$, in addition, can be related to an integral sum ($I_{SUM}$) that can also depend on an accumulation of past errors. As illustrated by the process 700, in some embodiments, $D_{TERM}$ can be set to 0 during the process 700.

$PID_{OUT}$ can be set to permissibly range from 0 to 100 so that 0 corresponds to a 0% duty cycle PWM control signal (for example, causing positive pressure to be supplied at a minimum level such as providing no positive pressure), 25 corresponds to a 25% duty cycle PWM control signal (for example, causing positive pressure to be supplied at a level 25% of a maximum level), 50 corresponds to a 50% duty cycle PWM control signal (for example, causing positive pressure to be supplied at a level 50% of a maximum level), 75 corresponds to a 75% duty cycle PWM control signal (for example, causing positive pressure to be supplied at a level 75% of a maximum level), and 100 corresponds to a 100% duty cycle PWM control signal (for example, causing positive pressure to be supplied at a maximum level). In one implementation, for instance, 0 may correspond to a 0% duty cycle PWM control signal and cause a valve like the valve 392 to remain fully open 0% of the time and fully closed 100% of the time, 25 may correspond to a 25% duty cycle PWM control signal and cause a valve like the valve 392 to remain fully open 25% of the time and fully closed 75% of the time, and 100 may correspond to a 100% duty cycle PWM control signal and cause a valve like the valve 392 to remain fully open 100% of the time and fully closed 0% of the time.

At block 702, the process 700 can determine whether a measured pressure ($P_{MEASURED}$) in the flow path is below a low vacuum threshold ($T_{LOW}$). The measured pressure can be a pressure measured by a pressure sensor positioned at or near an inlet of a pump assembly, such as the pump assembly 230, or in any other suitable place or places in the fluid flow path. If the measured pressure exceeds the low vacuum threshold, at block 704, the process 700 can set $I_{SUM}$ to be 0 and $PID_{OUT}$ to be 0, and the process 700 can end by returning the value of $PID_{OUT}$.

If the measured pressure does not exceed the low vacuum threshold, the process 700 can transition to block 706, where the process 700 can set ERROR to be a difference between the measured pressure and a pressure setpoint and set $P_{TERM}$ to be a proportional gain ($K_p$) times ERROR. The pressure setpoint can be set, for example, by a user of a pump assembly by setting a desired pressure or a mode of operation that corresponds to the pressure setpoint. In some embodiments, the proportional gain can be set at pump assembly manufacture or during a test operation of a pump assembly using one or more control loop tuning approaches. The proportional gain can, for instance, be set to a value ranging from 0 to 1, ranging from 0.3 to 0.9, ranging from 0.5 to 0.7, or to 0.6.

The process can transition to block 708, where the process 700 can determine whether $P_{TERM}$ equals or exceeds 100. If $P_{TERM}$ equals or exceeds 100, at block 710, the process 700 can set $I_{SUM}$ to be 0 and $PID_{OUT}$ to be 100, and the process 700 can end by returning the value of $PID_{OUT}$. If $P_{TERM}$ does not equal or exceed 100, the process 700 can transition to block 712, where the process 700 can determine whether ERROR is below 0. If ERROR is not below 0, the process 700 can set $I_{SUM}$ to be a sum of $I_{SUM}$ and 2 times ERROR at block 714. If ERROR is below 0, the process 700 can set $I_{SUM}$ to be a sum of $I_{SUM}$ and ERROR at block 716. The process 700 can transition from block 714 or 716 to block 718, where the process 700 can determine whether $I_{SUM}$ is less than 0. If $I_{SUM}$ is less than 0, at block 720, the process 700 can set $I_{SUM}$ to be 0 and $PID_{OUT}$ to be $P_{TERM}$ at block 720, and the process 700 can end by returning the value of $PID_{OUT}$.

If $I_{SUM}$ is not less than 0, the process 700 can transition to block 722, where the process 700 can set $I_{TERM}$ to be an integral gain ($K_I$) times $I_{SUM}$ and set $PID_{OUT}$ to be a sum of $P_{TERM}$ and $I_{TERM}$. In some embodiments, the proportional gain can be set to a value ranging from 0 to 1, ranging from 0.0001 to 0.0003, or to 0,0002. The process 700 can transition to block 724, where the process 700 can determine whether $PID_{OUT}$ exceeds 100. If $PID_{OUT}$ does not exceed 100, process 700 can end by returning the value of $PID_{OUT}$. If $PID_{OUT}$ exceeds 100, the process can transition to block 726, where the process 700 can scale $I_{SUM}$ (e.g., by an amount depending on or proportional to the amount that $PID_{OUT}$ exceeds 100) and set $PID_{OUT}$ to be 100, and the process 700 can end by returning the value of $PID_{OUT}$.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure therapy to a wound, the apparatus comprising:
   a source of negative pressure configured to be in fluidic communication with a wound dressing via a flow path to the wound dressing, the source of negative pressure configured to provide negative pressure under the wound dressing when the wound dressing is placed over a wound;
   a valve configured to control supply of positive pressure from a source of positive pressure to the wound dressing,
   wherein the valve, the source of positive pressure, and the source of negative pressure are positioned pneumatically in series in the flow path to the wound dressing so that the valve and the source of positive pressure are configured to provide positive pressure via the flow path to the wound dressing and the source of negative pressure is configured to provide negative pressure via the flow path to the wound dressing; and
   a controller configured to:
      operate the source of negative pressure to supply negative pressure via the flow path to the wound dressing for provision of negative pressure therapy,
      determine a pressure difference between a pressure under the wound dressing and a pressure setting,
      generate a control signal according at least to the pressure difference, and
      operate the valve using the control signal to vary an amount of positive pressure supplied via the flow path to the wound dressing so that the pressure under the wound dressing reaches the pressure setting during provision of negative pressure therapy.

2. The apparatus of claim 1, wherein the controller is configured to operate the valve to vary the amount of positive pressure when the controller applies intermittent negative pressure wound therapy to the wound.

3. The apparatus of claim 1, wherein the control signal is a pulse-width modulation (PWM) signal, and the controller is configured to vary a duty cycle of the PWM signal to operate the valve to vary the amount of positive pressure supplied via the flow path to the wound dressing.

4. The apparatus of claim 1, wherein the controller is configured to generate the control signal using a proportional-integral-derivative (PID) calculation, and an error of the PID calculation is the pressure difference.

5. The apparatus of claim 4, wherein the controller is configured to:
   at a first time, determine that an accumulated error of the PID calculation is negative, and
   set an integral term of the PID calculation to be 0 and the accumulated error to be 0 in response to a determination that the accumulated error is negative.

6. The apparatus of claim 4, wherein the controller is configured to:
   at a first time, determine that the error is negative, and
   set an accumulated error of the PID calculation to be greater than a sum of the accumulated error and the error in response to a determination that the error is negative.

7. The apparatus of claim 1, wherein the valve is positioned before an exhaust for the source of negative pressure.

8. The apparatus of claim 1, wherein the valve is a solenoid valve.

9. The apparatus of claim 1, wherein the flow path to the wound dressing comprises a common line to the wound dressing, and the valve and the source of positive pressure are configured to provide positive pressure via the common line to the wound dressing and the source of negative pressure is configured to provide negative pressure via the common line to the wound dressing.

10. The apparatus of claim 1, wherein the valve is configured to control supply of positive pressure from an exhaust connected to an atmospheric pressure or a pressure greater than atmospheric pressure.

11. The apparatus of claim 1, wherein the pressure under the wound dressing is equal to a pressure in the flow path to the wound dressing.

12. A method for applying negative pressure therapy to a wound, the method comprising:
 providing, by a source of negative pressure, negative pressure via a flow path to a wound dressing placed over a wound for provision of negative pressure therapy;
 determining a pressure difference between a pressure under the wound dressing and a pressure setting;
 generating a control signal according at least to the pressure difference; and
 operating a valve using the control signal to vary an amount of positive pressure supplied via the flow path to the wound dressing so that the pressure under the wound dressing reaches the pressure setting during provision of negative pressure therapy, the valve controlling supply of positive pressure from a source of positive pressure to the wound dressing,
 wherein the valve, the source of positive pressure, and the source of negative pressure, are positioned pneumatically in series in the flow path to the wound dressing so that the valve and the source of positive pressure provide positive pressure via the flow path to the wound dressing and the source of negative pressure provides negative pressure via the flow path to the wound dressing.

13. The method of claim 12, wherein said operating the valve to vary the amount of positive pressure is performed when intermittent negative pressure wound therapy is being applied to the wound.

14. The method of claim 12, wherein the control signal is a pulse-width modulation (PWM) signal, and said operating the valve to vary the amount of positive pressure is performed by varying a duty cycle of the PWM signal.

15. The method of claim 14, wherein said generating the control signal comprises generating the control signal using a proportional-integral-derivative (PID) calculation, and an error of the PID calculation is the pressure difference.

16. The method of claim 12, wherein the valve is positioned before an exhaust for the source of negative pressure.

17. The method of claim 12, wherein the valve is a solenoid valve.

18. The method of claim 12, where the flow path to the wound dressing comprises a common line to the wound dressing, and said providing negative pressure comprises providing negative pressure via the common line to the wound dressing and said operating the valve comprises operating the valve using the control signal to vary the amount of positive pressure supplied via the common line to the wound dressing.

19. The method of claim 12, wherein the valve controls supply of positive pressure from an exhaust connected to an atmospheric pressure or a grater pressure greater than atmospheric pressure.

20. The method of claim 12, wherein the pressure under the wound dressing is equal to a pressure in the flow path to the wound dressing.

* * * * *